United States Patent
Furukawa et al.

[11] Patent Number: 6,020,503
[45] Date of Patent: Feb. 1, 2000

[54] PROCESS FOR PRODUCING 1,4-BENZODIOXANE DERIVATIVES

[75] Inventors: Yoshiro Furukawa, Osaka; Kazuhiro Kitaori, Itami; Shouhei Matsui, Amagasaki, all of Japan

[73] Assignee: Daiso Co., Ltd., Osaka, Japan

[21] Appl. No.: 09/147,503

[22] PCT Filed: May 12, 1998

[86] PCT No.: PCT/JP98/02081

§ 371 Date: Jan. 11, 1999

§ 102(e) Date: Jan. 11, 1999

[87] PCT Pub. No.: WO98/51680

PCT Pub. Date: Nov. 19, 1998

[30] Foreign Application Priority Data

May 12, 1997 [JP] Japan ................................. 9-120849

[51] Int. Cl.[7] ..................... C07D 319/14; C07D 319/06; C07D 309/00
[52] U.S. Cl. .......................... 549/361; 549/358; 549/359; 549/366; 549/374
[58] Field of Search .................... 549/358, 359, 549/362, 366, 374

[56] References Cited

FOREIGN PATENT DOCUMENTS

| | | |
|---|---|---|
| 0 221 725 B1 | 8/1990 | European Pat. Off. |
| 0 841 334 A1 | 5/1998 | European Pat. Off. |
| 62-174068 | 10/1985 | Japan |
| 06009613 | 1/1994 | Japan |
| 8-325260 | 12/1996 | Japan |
| 10045746 | 2/1998 | Japan |
| WO96/30360 | 7/1997 | WIPO |

OTHER PUBLICATIONS

*II Farmaco Scientific Edition,* vol. XLIII, Supp. To No. 12, Dec. 1988, "Dedicated to III Meeting Heterocyclic Structures in the Medicinal Chemistry Research", May 1988.

Nelson et al., *J.C.S. Chem. Comm.,* "Absolute Configuration of 2–Alkylaminomethylbenzodioxans, Competitive α–Adrenergic Antagonists", 1976.

Willard et al., *J. Org. Chem.,* "Potential Diuretic–β–Adrenergic Blocking Agents: Synthesis of 3–[2–[(1,1–Dimethylethyl)amino]–1–hydroxyethyl]–1, 4–dioxino[2,3–g]quinolines", 1981, 46, 3846–3852.

*Primary Examiner*—Amelia Owens
*Attorney, Agent, or Firm*—Jacobson, Price, Holman & Stern, PLLC

[57] ABSTRACT

An industrial method for preparation of a 1,4-benzodioxane derivative (1), which comprises reacting a diol compound (2) with a carbonating agent to prepare a carbonate compound (3) and after removal of the protective group, cyclizing it by heating or by treating with a base or a fluoride salt.

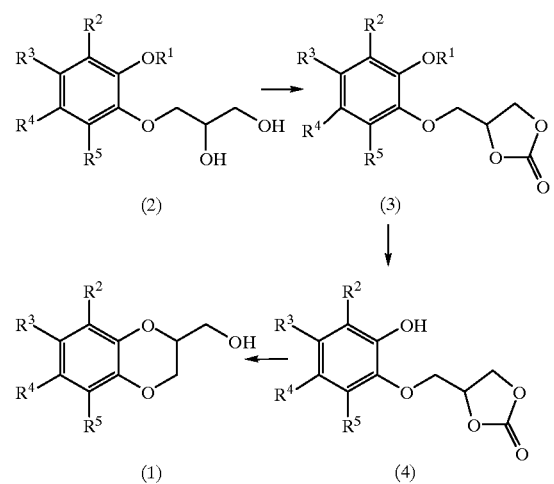

21 Claims, No Drawings

PROCESS FOR PRODUCING 1,4-BENZODIOXANE DERIVATIVES

This application is a 371 of PCT/JP98/02081 filed May 12, 1998.

TECHNICAL FIELD

The present invention relates to a process for preparation of a 1,4-benzodioxane derivative useful for an intermediate of circulatory drugs and drugs for psychoneurosis which are α and β-adrenergic antagonists.

BACKGROUND ART

A 1,4-benzodioxane derivative is used for an intermediate for preparation of circulatory drugs and drugs for psychoneurosis which are α- and β-adrenergic antagonist-activity and its various kind of processes are known. For example, the method by reacting a catechol derivative with glycidyl tosylate in the presence of sodium hydride (Japanese patent publication No.6-9613(1994)) or the method by reacting a catechol derivative with epichlorohydrin in the presence of pyridine (J. Org. Chem. 46,3846(1981)) is known. A method is also known to make a 1,4-benzodioxane skeleton by reacting a catechol derivative with glycerol 1-tosylate acetonide and, after removing the protective group, the acetonide, by introducing two tosyl group onto it and then by isolating it, and further by cyclizing it (J. Chem. Soc., Chem. Commun., 921(1976)).

DISCLOSURE OF INVENTION

Among the above known methods, besides the method comprising use of glycidyl tosylate is costly because of expense of its compound, the epoxy group is also reduced on the deprotection by hydrogenolysis and the yield decreases. In the method comprising the use of epichlorohydrin, the excess of epichlorohydrin and dichloropropanediol as a by-product must be eliminated by their evaporation with xylene, and the hydrochloric acid and acetic acid used must be eliminated by evaporation with ethanol and therefore, such procedures are troublesome. Moreover, the reaction is carried out under reflux of piperidine or hydrochloric acid. Accordingly, a compound with substituents which are unstable to an acid or a base can not be used. When using an optically active epichlorohydrin, racemization occurs and an optically pure product cannot be obtained. In the method comprising the reaction of a catechol derivative with glycerol 1-tosylate acetonide, the resulting ditosylated product must be separated after tosylation and therefore, yield of the ditosylated product is 55% or lower. These methods have many disadvantages in application of an industrial scale. An improved method has been desired.

The present inventors, taking into the consideration of the above fact, extensively engaged in study to find an improved method for preparation of a 1,4-benzodioxane derivative. As a result it was found that after carbonating a phenoxypropanediol compound, by cyclizing the resulting product by heating or by treating with a base, the desired 1,4-benzodioxane derivative is favourably obtained in an industrial scale.

The present invention relates to a process for preparation of a 1,4-benzodioxane derivative shown by the following formula (1), which is characterized in reacting a diol compound as shown by the following formula (2) with a carbonating agent to prepare a carbonate compound shown by the following formula (3), removing a protective group of the carbonate compound to prepare a phenol derivative shown by the following formula (4), and then cyclizing the phenol derivative by heat-treatment or by treatment with a base or a fluoride salt.

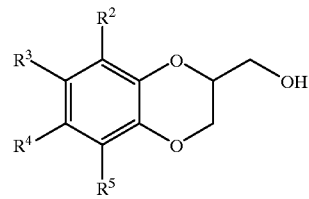

(1)

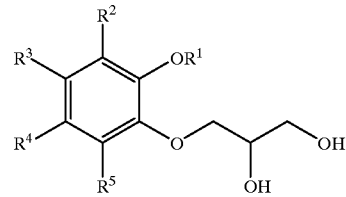

(2)

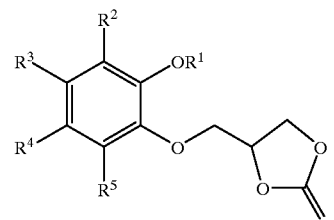

(3)

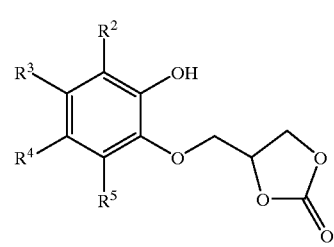

(4)

In the above formulae (1)–(4), $R^1$ is a protective group of hydroxy, $R^2$, $R^3$, $R^4$ and $R^5$ are the same or different and hydrogen, halogen, hydroxy, nitro, cyano, formyl, hydroxycarbonyl, alkoxycarbonyloxy in which the alkyl portion has 1–4 carbon atoms, alkyl having 1–4 carbon atoms, alkoxy having 1–4 carbon atoms, haloalkyl having 1–4 carbon atoms, N,N-dialkylamino in which the alkyl has 1–4 carbon atoms, alkylcarbonyl in which the alkyl portion has 1–4 carbon atoms, alkoxycarbonyl in which the alkyl portion has 1–4 carbon atoms, or phenyl which may be substituted by one or more alkyls having 1–4 carbon atoms, and adjacent two groups of $R^2$, $R^3$, $R^4$ and $R^5$ may constitute a methylenedioxy, or may constitute a benzene ring via carbon atoms on which said groups bind, and $R^2$ and $OR^1$ may constitute a methylenedioxy, an isopropylidenedioxy, a cyclohexylidenedioxy or a diphenylmethylenedioxy.

BEST MODE FOR CARRYING OUT THE INVENTION

The present invention is described in detail along with the following reaction scheme.

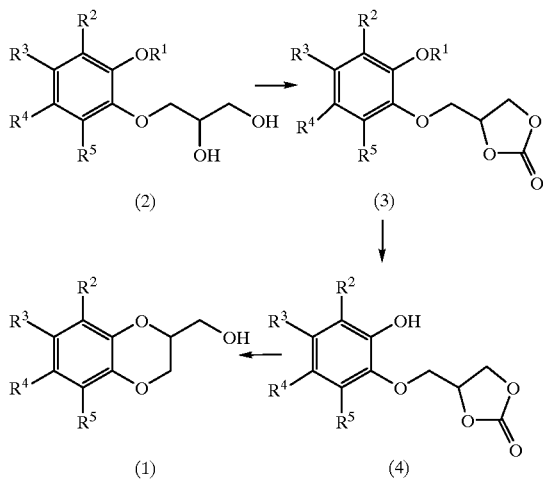

$R^1$, $R^2$, $R^3$, $R^4$ and $R^5$ in the above formulae are the same as defined above.

First, a carbonate compound (3) is obtained by reacting a diol compound (2) with a carbonating agent.

Examples of the carbonating agent are a carbonic acid ester, such as dimethyl carbonate, diethyl carbonate, dipropyl carbonate, diallyl carbonate, allyl methyl carbonate, diphenyl carbonate, bis(4-nitrophenyl) carbonate, ethylene carbonate, etc., a chlorocarbonic acid ester, such as methyl chloroformate, ethyl chloroformate, 1-chloroethyl chloroformate, 2-chloroethyl chloroformate, 2-bromoethyl chloroformate, 2,2,2-trichloroethyl chloroformate, 1,2,2,2-tetrachloroethyl chloroformate, propyl chloroformate, isopropyl chloroformate, butyl chloroformate, 4-chlorobutyl chloroformate, isobutyl chloroformate, hexyl chloroformate, octyl chloroformate, vinyl chloroformate, allyl chloroformate, etc., a carbonic acid ester having a heterocycle as a removing group, such as N,N'-carbonyldiimidazole, N,N'-disuccinimidyl carbonate, etc., phosgene, and its oligomer, such as trichloromethyl chloroformate, bis-trichloromethyl carbonate, etc.

The above reaction is carried out in a solvent or in the absence of a solvent. Examples of the solvent are a dipolar aprotic solvent such as N,N-dimethylformamide, dimethyl sulfoxide, sulfolane, hexamethylphosphoramide, etc., an ether, such as tetrahydrofuran, dioxane, t-butyl methyl ether, diethyl ether, etc., a chlorinated compound, such as methylene chloride, chloroform, dichloroethane, etc., an aromatic hydrocarbon, such as benzene, toluene, etc., a nitrile, such as acetonitrile, butyronitrile, etc., and water.

The reaction is smoothly carried out by removing the resulting alcohol or by absorbing it into molecular sieves, etc. When hydrochloric acid occurs on the way of the reaction on a kind of a carbonating agent used, the reaction is carried out in the presence of a base. By doing so, the reaction mixture is not only neutralized, but the reaction is also smoothly carried out.

Examples of the base are a trialkylamine having 1–6 carbon atoms, such as trimethylamine, triethylamine, ethyldiisopropylamine, etc., a tertiary amine substituted by groups selected from an alkyl having 1–4 carbon atoms and a phenyl, such as N,N-dimethylaniline, N,N-diethylaniline, etc., an organic base containing a nitrogen atom, such as pyridine, picoline, lutidine, etc., an alkali metal or alkaline earth metal salt of a lower alcohol having 1–4 carbon atoms, such as sodium methoxide, sodium ethoxide, etc., an inorganic base, such as an alkali metal hydride, an alkali metal or alkaline earth metal hydroxide, hydrogen carbonate or carbonate, etc. Examples of an inorganic base are sodium hydride, sodium hydroxide, potassium hydroxide, calcium hydroxide, sodium hydrogen carbonate, potassium hydrogen carbonate, sodium carbonate, potassium carbonate, magnesium carbonate, calcium carbonate and so on.

When there is used a carbonating agent which does not occur hydrochloric acid on the way of the reaction, such as dimethyl carbonate or diethyl carbonate, the reaction is smoothly carried out in the presence of catalytic amount of a trialkyl amine having 1–6 carbon atoms, such as trimethylamine, triethylamine, ethyldiisopropylamine, etc., a tertiary amine substituted by groups selected from an alkyl having 1–4 carbon atoms and a phenyl, such as N,N-dimethylaniline, N,N-diethylaniline, etc., an organic base containing a nitrogen atom, such as pyridine, picoline, lutidine, etc., an alkali metal or alkaline earth metal salt of a lower alkanol having 1–4 carbon atoms, such as sodium methoxide, sodium ethoxide, etc., an inorganic base, such as an alkali metal hydride, an alkali metal or alkaline earth metal hydroxide, hydrogen carbonate, carbonate, etc.

Next, removal of the protective group, $R^1$ of a carbonate compound (3) is carried out.

The protective group, $R^1$ is not limited as long as it does not affect the reaction.

When a protective group is benzyl, allyl or benzyloxycarbonyl, the protected compound is subjected to catalytic hydrogenation by using hydrogen gas or ammonium formate in the presence of palladium-carbon or Raney nickel in an organic solvent, such as methanol, ethanol, ethyl acetate, etc. or its mixture with water to remove the protective group.

When a protective group is o-nitrobenzyl, the protected compound is subjected to radiation in an organic solvent, such as methanol or ethanol to remove it. When a protective group is t-butyldimethylsilyl, it is deprotected by using a salt of a fluoride, such as sodium fluoride, potassium fluoride, tetrabutylammonium fluoride, etc. in an organic solvent, such as dimethylformamide, tetrahydrofuran or its mixture with water.

When a protective group constituted with $R^2$ and $OR^1$ is methylenedioxy, isopropylidenedioxy, cyclohexylidenedioxy or diphenylmethylenedioxy, the protected compound is usually deprotected in acidic conditions conventionally used in elimination of such a protective group.

When a compound (3) in which $R^1$ is allyl and either or both of $R^2$ and $R^4$ are hydrogen (positions either or both of 3 and 5 on the benzene ring are hydrogen) is subjected to so-called Claisen-rearrangement reaction by heating or by treatment in the presence of Lewis acid, the elimination of $R^1$ and the rearrangement of the $R^1$ into position 3 or 5 of the benzene ring occur simultaneously.

The above heat-treatment is carried out in a solvent or in the absence of a solvent. Examples of the solvent are an aromatic hydrocarbon, such as benzene, toluene, xylene, mesitylene, a dipolar aprotic solvent such as N,N-dimethylformamide, dimethyl sulfoxide, sulfolane, hexamethylphosphoramide, etc., a ketone, such as diisobutyl ketone, dipropyl ketone, methyl pentyl ketone, butyl methyl ketone, acetone, ethyl methyl ketone, methyl propyl ketone, diethyl ketone, etc., an ether, such as diethylene glycol dimethyl ether, diethylene glycol diethyl ether, dibutyl ether, dioxane, tetrahydrofuran, t-butyl methyl ether, diethyl ether, etc., a chlorinated compound, such as methylene chloride, chloroform, dichloroethane, etc., a nitrile, such as acetonitrile, butyronitrile, etc. This reaction is carried out at 0–250° C., preferably 20–200° C. at atmospheric pressure or under the pressure. The rearrangement of $R^1$ occurs first at position 3, and in lapse of time the amount of a phenol derivative rearranged at position 5 increases.

In case of Claisen rearrangement reaction under Lewis acid, examples of Lewis acid are a boron compound, such as boron trichloride, boron trifluoride, boron tribromide, etc. and its complex with acetic acid or an ether, an organic aluminum compound, such as triethylaluminum, chlorodiethyl aluminum, chlorodiisobutylaluminum, dichloroethylaluminum, aluminum(III) chloride, etc., a Grignard reagent, such as phenylmagnesium bromide etc., antimony (v) chloride, a stannic(IV) compound, such as stannic(IV) chloride etc., a zinc(II) compound, such as zinc(II) chloride, zinc(II) bromide, etc., a titanium(IV) compound, such as titanium(IV) tetrachloride etc., a silver(I) salt, such as silver(I) trifluoroborate, silver trifluoroacetate, etc., a mercuric(II) compound, such as mercuric(II) trifluoroacetate etc. Among Lewis acids, chlorodiethyl aluminum is especially preferable. The amount of Lewis acid is 0.3–10 mol equivalents to a carbonate compound (3), preferably 1–3 mol equivalents. Examples of the solvent used in this reaction are a chlorinated compound, such as methylene chloride, chloroform, carbon tetrachloride, chlorobenzene, etc., an aromatic hydrocarbon, such as benzene, toluene, xylene, etc., a satulated hydrocarbon, such as hexane, heptane, decahydronaphthalene, etc., an ether, such as diethyl ether etc. Methylene chloride is preferable. The reaction temparature is −78–120° C., preferably room temparature −42° C.

A phenol derivative (4) prepared above is cyclized by heat-treatment or by treatment with a base or a fluoride salt to prepare 1,4-benzodioxane derivative (1).

The ring-closure reaction is carried out by heat-treatment in the presence or absence of a solvent. Examples of the solvent are a dipolar aprotic solvent such as N,N-dimethylformamide, dimethyl sulfoxide, sulfolane, hexamethylphosphoramide, etc., a ketone, such as diisobutyl ketone, dipropyl ketone, methyl pentyl ketone, butyl methyl ketone, acetone, ethyl methyl ketone, methyl propyl ketone, diethyl ketone, etc., an ether, such as diethylene glycol dimethyl ether, diethylene glycol diethyl ether, dibutyl ether, dioxane, tetrahydrofuran, t-butyl methyl ether, diethyl ether, etc., a chlorinated compound, such as methylene chloride, chloroform, dichloroethane, etc., an aromatic hydrocarbon, such as benzene, toluene, xylene, etc., a nitrile, such as acetonitrile, butyronitrile, etc. This reaction is carried out at 0–250° C., preferably 30–200° C. at atmospheric pressure or under the pressure.

The ring-closure reaction is also carried out by treatment with a base, in the presence or absence of a solvent. Examples of the solvent are a dipolar aprotic solvent such as N,N-dimethylformamide, dimethyl sulfoxide, sulfolane, hexamethylphosphoramide, etc., a ketone, such as diisobutyl ketone, dipropyl ketone, methyl pentyl ketone, butyl methyl ketone, acetone, ethyl methyl ketone, methyl propyl ketone, diethyl ketone, etc., an ether, such as diethylene glycol dimethyl ether, diethylene glycol diethyl ether(diglyme), dibutyl ether, dioxane, tetrahydrofuran, t-butyl methyl ether, diethyl ether, etc., a chlorinated compound, such as methylene chloride, chloroform, dichloroethane, etc., an aromatic hydrocarbon, such as benzene, toluene, xylene, etc., a nitrile, such as acetonitrile, butyronitrile, etc.

Examples of the base are a trialkylamine, such as trimethylamine, triethylamine, ethyldiisopropylamine, trioctylamine, etc., a tertiary amine substituted by an alkyl having 1–4 carbon atoms and a phenyl, such as N,N-dimethylaniline, N,N-diethylaniline, etc., an organic base containing a nitrogen atom, such as pyridine, picoline, lutidine, etc., an alkali metal or alkaline earth metal salt of a lower alcohol having 1–4 carbon atoms, such as sodium methoxide, sodium ethoxide, etc., an inorganic base, such as an alkali metal hydride, an alkali metal or alkaline earth metal hydroxide, hydrogen carbonate or carbonate, etc. Examples of the inorganic base are sodium hydride, sodium hydroxide, potassium hydroxide, calcium hydroxide, sodium hydrogen carbonate, potassium hydrogen carbonate, sodium carbonate, potassium carbonate, magnesium carbonate, calcium carbonate and so on. Among them, an alkali metal hydride and a trialkylamine are preferable. Amount of the base is 0.005–10 mol to a compound(4), preferably 0.01–5 mol. The reaction temperature is −50–250° C., preferably 0–150° C.

The ring-closure reaction of a phenol compound (4) can be also carried out by treatment with a fluoride salt.

The fluoride salts are preferably an alkali metal salt and an alkaline metal salt and they are used solely or in a mixture of them. They are also used with a support. Examples of the fluoride salt are sodium fluoride, potassium fluoride, cesium fluoride, magnesium fluoride and calcium fluoride. Potassium fluoride, cesium fluoride and a mixture thereof are preferably used. Examples of the support are celite, alumina, silica gel, molecular sieve and its modified one. This reaction is carried out in the presence or absence of a solvent. Examples of the solvent are a dipolar aprotic solvent, such as N,N-dimethylformamide, dimethyl sulfoxide, sulfolane, hexamethylphosphoramide, etc., an ether, such as tetrahydrofuran, dioxane, t-butyl methyl ether, diethyl ether, etc., a chlorinated compound, such as methylene chloride, chloroform, dichloroethane, etc., an aromatic hydrocarbon, such as benzene, toluene, xylene, etc., a nitrile, such as acetonitrile, butyronitrile, etc., an ester, such as ethyl acetate, butyl acetate, etc. The amount of the fluoride salt is 0.005–10 mol to a compound (4), preferably 0.01–5 mol. This reaction is carried out at 0–250° C., preferably 30–150° C.

As mentioned above, when a carbonate compound (3) in which $R^1$ is allyl, either or both of $R^2$ and $R^4$ are hydrogen is subjected to so-called Claisen rearrangement reaction by heating or in the presence of Lewis acid, elimination and rearrangement of $R^1$ occur simultaneously to produce a phenol derivative (4). In case of heat-treatment, by further heating the resulting phenol derivative, it is simultaneously cyclized to prepare a 1,4-benzodioxane derivative.

The above reaction is carried out in the presence or absence of a solvent. Examples of the solvent are a dipolar aprotic solvent such as N,N-dimethylformamide, dimethyl sulfoxide, sulfolane, hexamethylphosphoramide, etc., a ketone, such as diisobutyl ketone, dipropyl ketone, methyl pentyl ketone, butyl methyl ketone, acetone, ethyl methyl ketone, methyl propyl ketone, diethyl ketone, etc., an ether, such as diethylene glycol dimethyl ether, diethylene glycol diethyl ether, dibutyl ether, dioxane, tetrahydrofuran, t-butyl methyl ether, diethyl ether, etc., a chlorinated compound, such as methylene chloride, chloroform, dichloroethane, etc., an aromatic hydrocarbon, such as benzene, toluene, xylene, etc., a nitrile, such as acetonitrile, butyronitrile, etc. The reaction proceeds by heating without a catalyst, but in the presence of a basic catalyst, the reaction proceeds smoothly without side-reaction.

As the base, there is used at least a base selected from a trialkylamine, such as trimethylamine, triethylamine, ethyldiisopropylamine, trioctylamine, etc., and a tertiary amine substituted by groups selected from an alkyl having 1–4 carbon atoms and a phenyl, such as N,N-dimethylaniline, N,N-diethylaniline, etc. There is also used an alkali metal hydride, an alkali metal or alkaline earth metal hydroxide, or an alkali metal or alkaline earth metal salt of a lower alkanol having 1–4 carbon atoms, e.g. sodium hydride, sodium hydroxide, potassium hydroxide, sodium methoxide, or sodium ethoxide. Among them, a trialkylamine is especially preferable. The amount of the base is 0.005–10 mol to a carbonate compound (3), preferably 0.01–5 mol. The reaction temperature is −50–250° C., preferably 0–200° C.

A compound (3) in which $R^1$ is allyl, is subjected to rearrangement reaction and the rearranged product is further subjected to ring-closure reaction to prepare a objective compound (1) in which $R^2$ or $R^4$ is allyl. This reaction is shown schematically as follows.

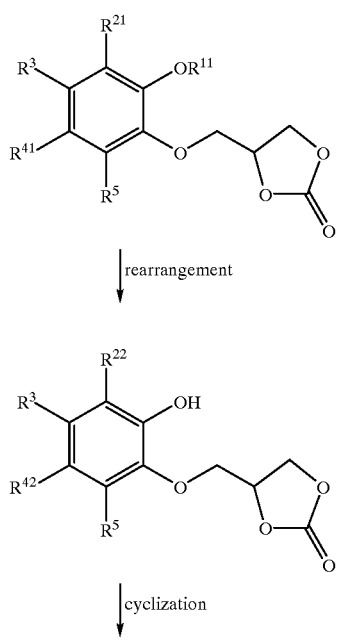

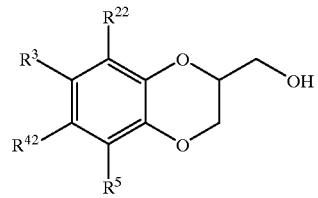

In the above formulae, $R^{11}$ is allyl, $R^{21}$, $R^{22}$, $R^{41}$, and $R^{42}$ are the same or different and are hydrogen, halogen, hydroxyl, nitro, cyano, formyl, hydroxycarbonyl, an alkoxycarbonyloxy in which the alkyl portion has 1–4 carbon atoms, an alkyl having 1–4 carbon atoms, an alkoxy having 1–4 carbon atoms, a haloalkyl having 1–4 carbon atoms, N,N-dialkylamino in which the alkyl has 1–4 carbon atoms, alkylcarbonyl in which the alkyl portion has 1–4 carbon atoms, an alkoxycarbonyl in which the alkyl portion has 1–4 carbon atoms, or a phenyl which may be substituted by one or more alkyls having 1–4 carbon atoms, provided that either or both of $R^{21}$ and $R^{41}$ are hydrogen, and either or both of $R^{22}$ and $R^{42}$ are allyl. And $R^3$ and $R^5$ are the same as defined above.

A diol compound (2) used as a starting material in this invention is prepared by a method shown by the following scheme.

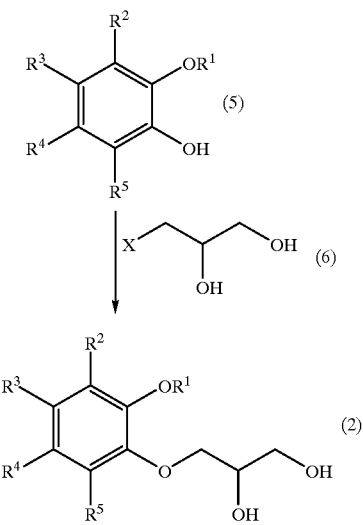

In the above formulae, $R^1$, $R^2$, $R^3$, and $R^5$ are the same as defined above, and X is hydrogen.

A diol compound (2) is prepared by reacting a catechol derivative (5) with a 3-halogeno-1,2-propanediol, preferably 3-chloro-1,2-propanediol or 3-bromo-1,2-propanediol in the presence of a base in a solvent.

Examples of the solvent are a dipolar aprotic solvent such as N,N-dimethylformamide, dimethyl sulfoxide, sulfolane, hexamethylphosphoramide, etc., an ether, such as tetrahydrofuran, dioxane, t-butyl methyl ether, diethyl ether, etc., a chlorinated compound, such as methylene chloride, chloroform, dichloroethane, etc., an aromatic hydrocarbon, such as benzene, toluene, xylene, etc., a nitrile, such as acetonitrile, butyronitrile, etc., a ketone, such as, acetone, ethyl methyl ketone, diisopropyl ketone, etc., methanol, ethanol, isopropanol, t-butanol, etc., and water.

Examples of the base are a trialkylamine, such as trimethylamine, triethylamine, ethyldiisopropylamine, trioctylamine, etc., and an inorganic base, such as an alkali metal or alkaline earth metal salt of an alkanol having 1–4 carbon atoms, e.g. sodium methoxide, sodium ethoxide, magnesium ethoxide, magnesium ethoxide, an alkali metal hydride, an alkali metal or alkaline earth metal hydroxide, an alkali metal or alkaline metal hydrogen carbonate or carbonate and so on. Examples of the inorganic base are sodium hydride, sodium hydroxide, potassium hydroxide, calcium hydroxide, sodium hydrogen carbonate, potassium hydrogen carbonate, sodium carbonate, potassium carbonate, magnesium carbonate, calcium carbonate, etc. Preferable examples are alkali metal hydroxides, such as sodium hydride, sodium methoxide, sodium ethoxide, sodium hydroxide, potassium hydroxide, sodium hydrogen carbonate, potassium hydrogen carbonate, sodium carbonate, potassium carbonate, etc. The amount of the base is 1–5 mol to a catechol derivative (5), preferably 1.1–3 mol. The amount of a 3-halogeno-1,2-propanediol is 1–5 mol to the catechol derivative, preferably 1.1–3 mol. The reaction temperature is −50–250° C., preferably 0–150° C.

A diol compound(2), a starting material in this invention can be also prepared by a known method, that is, by reacting a catechol derivative (5) with glycidol. However, glycidol is unstable and is readily polymerized. In contrast, a 3-halogeno-1,2-propanediol is stable and not costly. Therefore, as mentioned above, the method comprising use of this compound is industrially beneficial.

According to this invention, an optically active 1,4-dibenzodioxane derivative (1) is obtainable by using an optically active diol compound (2). Such an optically active diol compound is, for example, prepared by reacting a catechol derivative (5) with an optically active 3-halogeno-1,2-propanediol (6) under the same conditions mentioned above. When a 3-halogeno-1,2-propanediol with highly optical purity is used as a starting material, the racemization does not markedly occur during the reaction, and therefore, a 1,4-benzodioxane derivative (1) with highly optical purity is obtainable. A 3-halogeno-1,2-propanediol with highly optical purity (more than 98% ee), for example, is obtained by the method described in Japanese patent publication (2) 4-73998(1992) or 4-73999(1992) developed by this applicant. According to the process of this invention, a (S)-1,4-benzodioxane derivative (1) is obtained from a (R)-3-halogeno-1,2-propanediol, and a (R)-1,4-benzodioxane derivative (1) is obtained from a (S)-3-halogeno-1,2-propanediol.

This invention is in detail explained in the following examples, but this invention is not limited to the examples.

EXAMPLE 1

Sodium hydride (2.4 g, 0.06 mol) added to oil to be a 60% dispersion was washed with n-hexane, and anhydrous N,N-dimethylformamide (18 ml) was added thereto. To the resulting suspension was dropped 2-benzyloxy-3-methylphenol (6.39 g, 0.03 mol) in anhydrous N,N-dimethylformamide (10 ml) under ice cooling over a 15 minute period. After emission of gas was over, to the solution was dropped 3-chloro-1,2-propanediol (3.98 g, 0.036 mol) in anhydrous N,N-dimethlformamide (5 ml) over a 15 minute period at the same temperature. Then, the solution was stirred for 2 hours at 60° C. After the reaction was completed, water was added thereto and the mixture was extracted with ethyl acetate. The ethyl acetate layer was washed with water, dried over anhydrous magnesium sulfate and concentrated in vacuo to give a crude product as a pale yellow oil. The crude product was purified with column chromatography to give 8.28 g of a diol compound (2-1) ($R^1$ is benzyl, $R^2$ is methyl, and $R^3$, $R^4$ and $R^5$ are H) as a colorless oil: yield 96%.

$^1$H-NMR(CDCl$_3$): δ7.48–7.30(m,5H),6.99–6.78(m,3H), 4.96(s,2H), 4.10–3.97(m,3H),3.78–3.64(m,2H),2.34(s,3H)

The diol compound (2-1)(2.16 g, 7.5 mmol) was dissolved in dimethyl carbonate (30 ml) and to the solution was added sodium hydroxide (23 mg, 0.6 mmol). The mixture was heated for 30 minutes at 60° C. under nitrogen gas. And then the reaction temperature was raised to 90° C. to evaporate methanol. After the reaction was completed, dimethyl carbonate remaining was concentrated in vacuo and tetrahydrofuran (20 ml) was added thereto. By filtering off the insoluble materials and condensing the filtrate, there was obtained a crude product as a pale yellow solid (2.38 g). Further, the crude product was recrystallized to give 2.16 g of a carbonate compound (3-1) ($R^1$ is benzyl, $R^2$ is methyl, and $R^3$, $R^4$ and $R^5$ are H) as white crystals: yield 92.4%, m.p. 90–95.1° C.

$^1$H-NMR(CDCl$_3$): δ7.47–7.30(m,5H),6.99–6.77(m,3H), 5.01–4.88 (m,3H),4.51(t,2H),4.28(dd,1H),4.12(dd,1H),2.22 (s,3H)

The compound (3-1) (1.00 g, 3.2 mmol) was dissolved in methanol (30 ml) and the solution was subjected to hydrogenation under hydrogen in the presence of 200 mg of Pd-C (10 w/w %) at room temperature. After the reaction was completed, Pd-C was filtered off and the filtrate was condensed in vacuo to give a crude product as a white solid (715 mg). The crude product was recrystallized to give 689 mg of a phenol derivative (4-1) ($R^2$ is methyl, and $R^3$, $R^4$ and $R^5$ are H) as white crystals: yield 96.1%.

$^1$H-NMR(d$_6$-DMSO): δ8.43(br-s,1H),6.82–6.63(m,3H), 5.16–5.13 (m,1H),4.66–4.88(m,2H),4.26–4.16(m,2H),2.14 (s,3H)

Sodium hydride (10 mg, 2.31 mmol) added to oil to be a 60% dispersion was washed with n-hexane, and anhydrous dimethylformamide (3 ml) was added thereto. To the resulting suspension the above product (4-1) (462.8 mg, 2.1 mmol) dissolved in 5 ml of dimethylformamide was dropped over a 20 minute period under ice cooling under nitrogen gas. After emission of gas was over, the reaction mixture was stirred for 6 hours at 50° C. After the reaction was completed, water was added to the reaction mixture and it was extracted with ethyl acetate. The extract was washed with water, dried over anhydrous magnesium sulfate, concentrated in vacuo to give a crude product as a pale yellow oil (380 mg). The crude product was subjected to column chromatography to give 358 mg of 2-hydroxymethyl-8-methyl-1,4-benzodixane (1-1) ($R^2$ is methyl, and $R^3$, $R^4$ and $R^5$ are H) as a colorless oil: yield 94.7%.

$^1$H-NMR(CDCl$_3$): δ6.68(s,3H),4.51–3.68(m,5H),2.60–2.21 (br- s,1H),2.20(s,3H)

EXAMPLE 2

In the same manner as in the above example 1 except for by using 2-benzyloxy-3-fluorophenol instead of 2-benzyloxy-3-methylphenol and by using optically active (R)-3-chloro-1,2-propanediol (optical purity: 99.4% ee) as a diol compound, there was obtained (S)-2-hydroxymethyl-8-fluoro-1,4-benzodioxane(1-2) ($R^2$ is F, and $R^3$, $R^4$ and $R^5$ are H): yield 71%. The optical purity of this product was 99.3% ee by measurement with the chiral column OD (Daisel Chemical Industries Ltd.).

EXAMPLE 3

In the same manner as in the above example 2 except for by using 2-benzyloxy-3-methoxyphenol instead of 2-benzyloxy-3-fluorophenol, there was obtained (S)-2-hydroxymethyl-8-methoxy-1,4-benzodioxane(1-3)($R^2$ is $CH_3O$, and $R^3$, $R^4$ and $R^5$ are H): yield 83%. The optical purity of this product was 98.9% ee by measurement with the chiral column OD (Daisel Chemical Industries Ltd.).

EXAMPLE 4

In the same manner as in the above example 2 except for by using 2-benzyloxy-6-nitrophenol instead of 2-benzyloxy-3-fluorophenol, there was obtained (S)-2-hydroxymethyl-5-nitro-1,4-benzodioxane(1-4) ($R^5$ is $NO_2$, and $R^2$, $R^3$ and $R^4$ are H): yield 77%. The optical purity of this product was 98.9% ee by measurement with the chiral column OD (Daisel Chemical Industries Ltd.).

EXAMPLE 5

In the same manner as in the above example 2 except for by using 2-benzyloxy-5-ethoxycarbonylphenol instead of 2-benzyloxy-3-fluorophenol, there was obtained (S)-2-hydroxymethyl-6-ethoxycarbonyl-1,4-benzodioxane(1-5) ($R^4$ is EtOCO, and $R^2$, $R^3$ and $R^5$ are H): yield 65%. The optical purity of this product was 98.9% ee by measurement with the chiral column OD (Daisel Chemical Industries Ltd.).

EXAMPLE 6

In the same manner as in the above example 2 except for by using 2-benzyloxy-3-methylphenol instead of 2-benzyloxy-3-fluorophenol, there was obtained (S)-2-hydroxymethyl-8-methyl-1,4-benzodioxane(1-6) ($R^2$ is $CH_3$, $R^3$, $R^4$ and $R^5$ are H): yield 81%. The optical purity of this product was 98.9% ee by measurement with the chiral column OD (Daisel Chemical Industries Ltd.).

EXAMPLE 7

According to the method described in the above example 1 except for by using 2-allyloxyphenol (6.78 g) instead of 2-benzyloxy-3-methylphenol and by using optically active (R)-3-chloro-1,2-propanediol (optical purity: 99.4% ee) as a diol compound, there was obtained 10.1 g of a (S)-carbonate compound(3-2) ($R^1$ is allyl, and $R^{21}$, $R^3$ and $R^{41}$ are H): yield 89.3%, m.p. 76.3–79.7° C.

$^1$H-NMR(CDCl$_3$): δ7.02–6.87(m,4H),6.06(2q,1H),5.41 and 5.28 (m,2H),5.03–4.95(m,1H),4.66–4.53(m,4H),4.28–4.15 (m,1H)

The above (S)-compound(3-2) (2.5 g, 0.01 mol) was dissolved in diglyme (5 ml). Thereto trioctylamine (3.58 g, 0.01 mol) was added and the reaction was carried out in autoclave at 185° C. After the reaction was completed, diglyme and trioctylamine were removed in vacuo to give a crude product as a brown oil (2.15 g). The crude product was purified with column chromatography to give 1.75 g of (S)-2-hydroxymethyl-8-allyl-1,4-benzodioxane (1-7) ($R^{22}$ is allyl, and $R^3$, $R^{42}$ and $R^5$ are H) as a colorless oil: yield 85%. The optical purity of this product was 98.5% ee by measurement with the chiral column OD (Daisel Chemical Industries Ltd.).

$^1$H-NMR(CDCl$_3$): δ6.73(s,3H),6.03–5.88(m,1H),5.05 and 5.03 (m,2H),4.24–4.16(m,2H),4.07–4.00(m,1H),3.78(m, 2H),3.36–3.32(m,2H),2.70(br-s,1H)

The above (S)-compound(3-2)(1 g, 0.004 mol) was added to diisobutyl ketone (10 ml). The reaction was carried out in autoclave at 180° C. After the reaction was completed, the reaction mixture was cooled in ice, and resulting crystals were filtered and dried in vacuo to give 0.876 g of a (S)-phenol derivative (4-2)($R^{22}$ is allyl, and $R^3$, $R^{42}$ and $R^5$ are H) as pale yellow crystals: yield 87.6%, m.p. 150.9–155.1° C.

$^1$H-NMR(DMSO-d$_6$): δ8.50(br-s,1H),6.86–6.82(m,1H), 6.76–6.01 (m,2H),6.70(2q,1H),5.15–4.97(m,3H),4.54(ddd, 2H),4.23(m,2H), 3.33(m,2H)

The above (S)-compound(3-2)(990 mg, 4.0 mmol) was dissolved in methylene chloride (10 ml). Diethyl aluminum chloride (7 ml, 8.8 mol in 15% hexane) was dropped thereto and the solution was stirred for 1 hour at 42° C. After the reaction was completed, diluted hydrochloric acid was added to the reaction mixture, the mixture was extracted with ethyl acetate, washed with water and dried over anhydrous magnesium sulfate and concentrated in vacuo to give a crude product (955 mg). The crude product was purified with column chromatography to give 793 mg of (S)-compound (4-2) ($R^2$ is allyl, and $R^3$, $R^4$ and $R^5$ are H): yield 80%.

The above (S)-compound(4-2)(500 mg, 2 mmol) was dissolved in anhydrous dimethylformamide (5 ml), CsF (6.1 mg, 0.04 mmol) was added thereto under nitrogen gas and the mixture was stirred for 3 hours. After the reaction was completed, water was added to the reaction mixture, the mixture was extracted with ethyl acetate, washed with water and dried over anhydrous magnesium sulfate and concentrated in vacuo to give a crude product (432 mg) as a pale yellow oil. The crude product was purified with column chromatography to give 397 mg of (S)-2-hydroxymethyl-8-allyl-1,4-benzodioxane (1-7) ($R^2$ is allyl, and $R^3$, $R^4$ and $R^5$ are H) as a colorless oil: yield 96.4%. The optical purity of this product was 98.9% ee by measurement with the chiral column OD (Daisel Chemical Industries Ltd.).

Industrial Applicability

According to a process of this invention, a 1,4-benzodioxane derivative (1) can be obtained in good yield by using a starting material which is easily available and is not costly, and an optically active objective compound can be also obtained with highly optical purity. A 1,4-benzodioxane derivative (1) is useful for an intermediate of a medicine such as circulatory drugs and drugs for psychoneurosis which are α and β-adrenergic antagonists.

We claim:
1. A process for preparation of a 1,4-benzodioxane derivative represented by the following formula (1), which is characterized in cyclizing a phenol derivative represented by the following formula (4) by heat-treatment or by treatment with a base or a fluoride salt, (1)

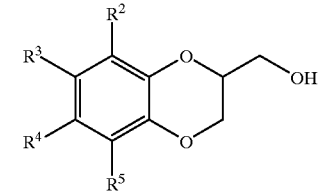

(2)

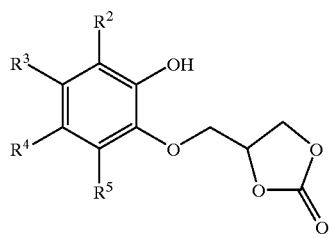

wherein in the above formulae (1) and (4), $R^2$, $R^3$, $R^4$ and $R^5$ are the same or different and are hydrogen, halogen, hydroxy, nitro, cyano, formyl, hydroxycarbonyl, alkoxycarbonyloxy in which the alkyl portion has 1–4 carbon atoms, alkyl having 1–4 carbon atoms, alkoxy having 1–4 carbon atoms, haloalkyl having 1–4 carbon atoms, N,N-dialkylamino in which the alkyl has 1–4 carbon atoms, alkylcarbonyl in which the alkyl portion has 1–4 carbon atoms, alkoxycarbonyl in which the alkyl portion has 1–4 carbon atoms, or phenyl which may be substituted by one or more alkyls having 1–4 carbon atoms, and adjacent two groups of $R^2$, $R^3$, $R^4$ and $R^5$ may constitute a methylenedioxy, or may constitute a benzene ring.

2. A process for preparation of a 1,4-benzodioxane derivative represented by the following formula (1), which is characterized in reacting a diol compound as shown by the following formula (2) with a carbonating agent to prepare a carbonate compound shown by the following formula (3), removing a protective group of the resulting carbonate compound to prepare a phenol derivative shown by the following formula (4), and then cyclizing the resulting phenol derivative by heat-treament or by treatment with a base or a fluoride salt, (1)

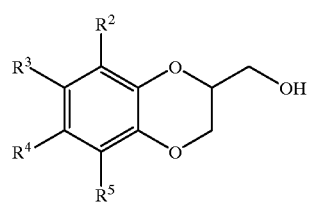

(2)

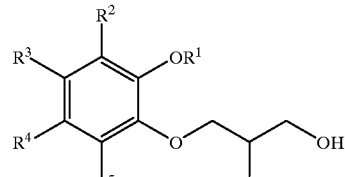

(3)

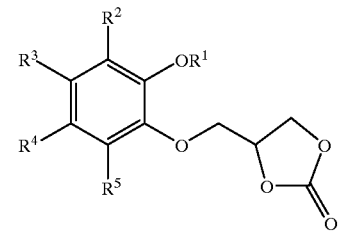

(4)

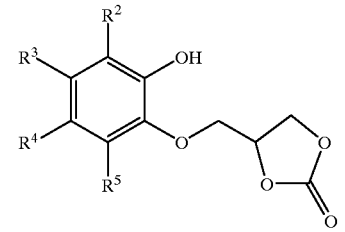

wherein in the above formula (1)–(4), $R^1$ is a protective group of hydroxy, $R^2$, $R^3$, $R^4$ and $R^5$ are the same or different and are hydrogen, halogen, hydroxy, nitro, cyano, formyl, hydroxycarbonyl, alkoxycarbonyloxy in which the alkyl portion has 1–4 carbon atoms, alkyl having 1–4 carbon atoms, alkoxy having 1–4 carbon atoms, haloalkyl having 1–4 carbon atoms, N,N-dialkylamino in which the alkyl has 1–4 carbon atoms, alkylcarbonyl in which the alkyl portion has 1–4 carbon atoms, alkoxycarbonyl in which the alkyl portion has 1–4 carbon atoms, or phenyl which may be substituted by one or more alkyls having 1–4 carbon atoms, and adjacent two groups of $R^2$, $R^3$, $R^4$ and $R^5$ may constitute a methylenedioxy, or may constitute a benzene ring via carbon atoms on which said groups bind, and $R^2$ and $OR^1$ may constitute a methylenedioxy, an isopropylidenedioxy, a cyclohexylidenedioxy or a diphenylmethylenedioxy.

3. The process for preparation of the 1,4-benzodioxane derivative (1) according to claim 2, wherein an optically active form is used as the diol compound (2) to prepare an optically active 1,4-benzodioxane derivative.

4. The process for preparation of the 1,4-benzodioxane derivative (1) according to claim 2, wherein the carbonating agent is a carbonic acid ester, phosgene or a phosgene oligomer.

5. The process for preparation of the 1,4-benzodioxane derivative (1) according to claim 2, wherein the protective group, $R^1$ is benzyl, allyl or benzyloxycarbonyl.

6. The process for preparation of the 1,4-benzodioxane derivative (1) according to claim 5, wherein removal of the protective group, $R^1$ on the carbonate compound (3) is carried out by catalytic hydrogenation.

7. The process for preparation of the 1,4-benzodioxane derivative (1) according to claim 1, wherein the phenol derivative (4) is cyclized by treating with a base.

8. The process for preparation of the 1,4-benzodioxane derivative (1) according to claim 7, wherein the base is an alkali metal hydride or trialkylamine.

9. The process for preparation of the 1,4-benzodioxane derivative (1) according to claim 1, wherein the phenol derivative (4) is cyclized by treating with a fluoride salt.

10. The process for preparation of the 1,4-benzodioxane derivative (1) according to claim 9, wherein the fluoride salt is an alkali metal fluoride or an alkaline earth metal fluoride.

11. The process for preparation of the 1,4-benzodioxane derivative (1) according to claim 10, wherein the alkali metal fluoride is potassium fluoride, cesium fluoride or a mixture thereof.

12. A process for preparation of a 1,4-benzodioxane derivative represented by the following formula (1a), which is characterized in subjecting a carbonate compound represented by the following formula (3a) to rearrangement reaction of the allyl group into position 3 or 5 on the benzene ring by heating or by treating in the presence of Lewis acid to prepare a phenol derivative represented by the following formula (4a), and then cyclizing the resulting phenol derivative by heat-treatment or by treatment with a base or a fluoride salt,

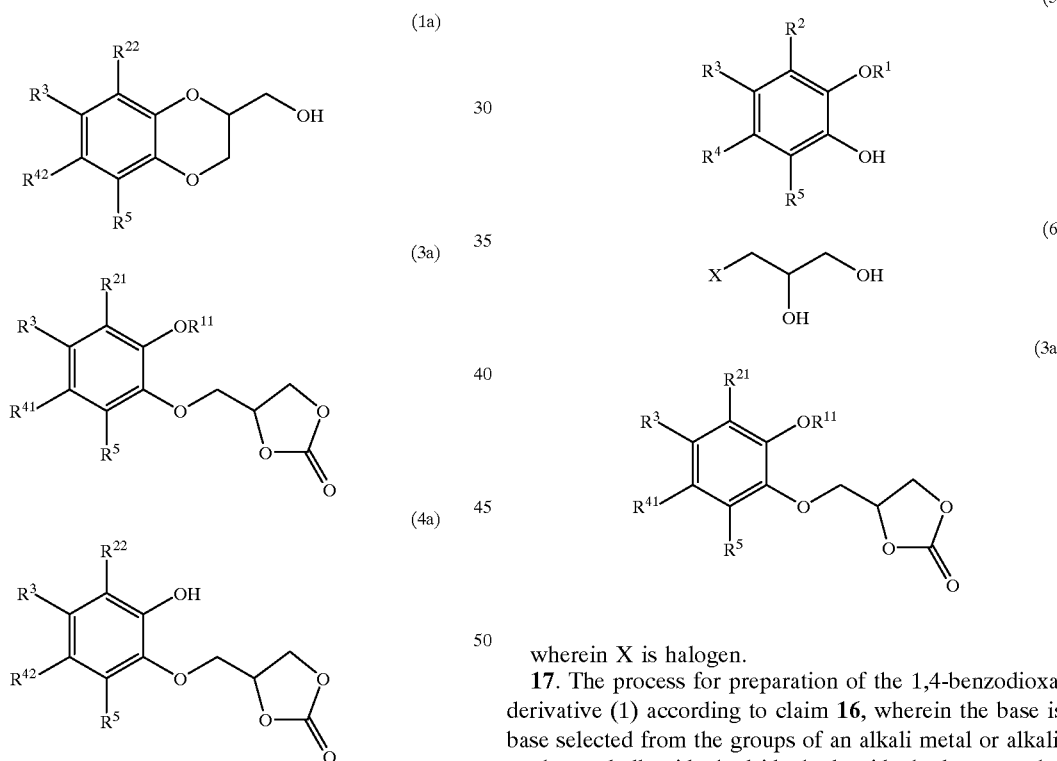

wherein in the above formula (1a), (3a) and (4a), $R^{11}$ is allyl, $R^{21}$, $R^{22}$, $R^3$, $R^{41}$, $R^{42}$ and $R^5$ are the same or different and are hydrogen, halogen, hydroxy, nitro, cyano, formyl, hydroxycarbonyl, alkoxycarbonyloxy in which the alkyl portion has 1–4 carbon atoms, alkyl having 1–4 carbon atoms, alkoxy having 1–4 carbon atoms, haloalkyl having 1–4 carbon atoms, N,N-dialkylamino in which the alkyl has 1–4 carbon atoms, alkylcarbonyl in which the alkyl portion has 1–4 carbon atoms, alkoxycarbonyl in which the alkyl portion has 1–4 carbon atoms, or phenyl which may be substituted by one or more alkyls having 1–4 carbon atoms, provided that either or both of $R^{21}$ and $R^{41}$ are hydrogen, and either or both of $R^{22}$ and $R^{42}$ are allyl.

13. The process for preparation of the 1,4-benzodioxane derivative (1a) according to claim 12, wherein the carbonate compound (3a) is subjected to rearrangement reaction of the allyl group into position 3 or 5 on the benzene by heating, and by further heating, cyclizing the resulting product.

14. The process for preparation of the 1,4-benzodioxane derivative (1a) according to claim 13, wherein the rearrangement reaction and ring-closure reaction are carried out by heating in the presence of a base.

15. The process for preparation of the 1,4-benzodioxane derivative (1a) according to claim 14, wherein the base is trialkylamine.

16. The process for preparation of the 1,4-benzodioxane derivative (1) according to claim 2, wherein the diol compound (2) is prepared by reacting a catechol derivative represented by the following formula (5) with a 3-halogeno-1,2-propanediol represented by the following formula (6) in the presence of a base,

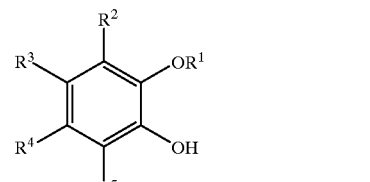

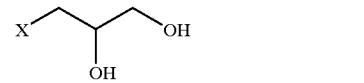

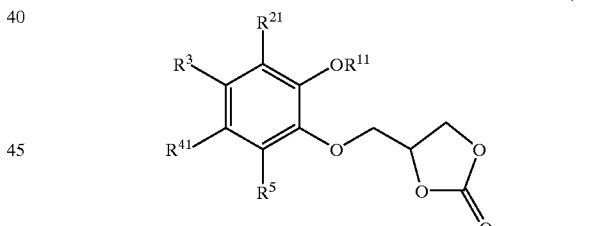

wherein X is halogen.

17. The process for preparation of the 1,4-benzodioxane derivative (1) according to claim 16, wherein the base is a base selected from the groups of an alkali metal or alkaline earth metal alkoxide, hydride, hydroxide, hydrogen carbonate and carbonate.

18. The process for preparation of the optically active 1,4-benzodioxane derivative (1) according to claim 16, wherein the 3-halogeno-1,2-propanediol(6) is an optically active form.

19. A process for preparation of a phenol derivative represented by the following formula (4a), which is characterized in subjecting a carbonate compound represented by the following formula (3a) to rearrangement reaction of the allyl group into position 3 or 5 on the benzene ring by heating or treating in the presence of Lewis acid, (4a)
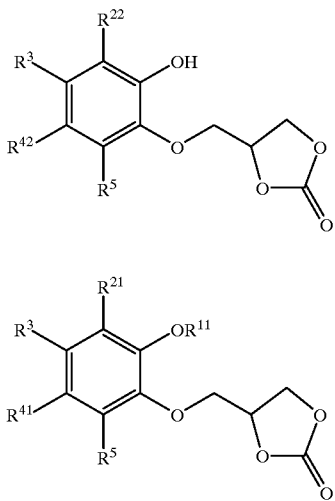

(3a)
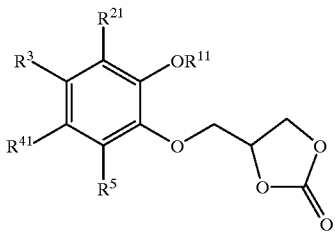

wherein in the above formulae (4a) and (3a), $R^{11}$ is allyl, $R^{21}$, $R^{22}$, $R^3$, $R^{41}$, $R^{42}$ and $R^5$ are the same or different and are hydrogen, halogen, hydroxy, nitro, cyano, formyl, hydroxycarbonyl, alkoxycarbonyloxy in which the alkyl portion has 1–4 carbon atoms, alkyl having 1–4 carbon atoms, alkoxy having 1–4 carbon atoms, haloalkyl having 1–4 carbon atoms, N,N-dialkylamino in which the alkyl has 1–4 carbon atoms, alkylcarbonyl in which the alkyl portion has 1–4 carbon atoms, alkoxycarbonyl in which the alkyl portion has 1–4 carbon atoms, or phenyl which may be substituted by one or more alkyls having 1–4 carbon atoms, provided that either or both of $R^{21}$ and $R^{41}$ are hydrogen, and either or both of $R^{22}$ and $R^{42}$ are allyl.

20. The process for preparation of the phenol derivative (4a) according to claim 19, wherein the carbonate compound is treated in the presence of Lewis acid.

21. The process for preparation of the optically active 1,4-benzodioxane derivative (1) according to claim 1, wherein the phenol derivative (4) is an optically active form.

* * * * *